(12) United States Patent
Bae et al.

(10) Patent No.: US 11,603,534 B2
(45) Date of Patent: Mar. 14, 2023

(54) PROMOTER AND USE THEREOF

(71) Applicant: CJ CHEILJEDANG CORPORATION, Seoul (KR)

(72) Inventors: Jee Yeon Bae, Seoul (KR); Chang Il Seo, Seoul (KR); Inhwa Yoo, Seoul (KR); Hye Ryun Yoo, Seoul (KR); So Young Kim, Seoul (KR); Yong Uk Shin, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/959,827

(22) PCT Filed: Mar. 15, 2019

(86) PCT No.: PCT/KR2019/003057
§ 371 (c)(1),
(2) Date: Jul. 2, 2020

(87) PCT Pub. No.: WO2019/182296
PCT Pub. Date: Sep. 26, 2019

(65) Prior Publication Data
US 2020/0407731 A1    Dec. 31, 2020

(30) Foreign Application Priority Data

Mar. 20, 2018   (KR) ........................ 10-2018-0032253

(51) Int. Cl.
| | |
|---|---|
| *C12P 13/08* | (2006.01) |
| *C12N 15/77* | (2006.01) |
| *C12N 15/67* | (2006.01) |
| *C12N 15/70* | (2006.01) |

(52) U.S. Cl.
CPC ............. *C12N 15/77* (2013.01); *C12N 15/67* (2013.01); *C12N 15/70* (2013.01)

(58) Field of Classification Search
None
See application file for complete search history.

(56) References Cited

U.S. PATENT DOCUMENTS

| 7,662,943 | B2 * | 2/2010 | Park ...................... C07K 14/34 |
| | | | 536/23.1 |
| 9,562,246 | B2 * | 2/2017 | Kim ..................... C12N 9/1077 |
| 2019/0185857 | A1 | 6/2019 | Lee et al. |

FOREIGN PATENT DOCUMENTS

| KR | 2006-0068505 A | 6/2006 |
| KR | 10-0725336 | 6/2007 |
| KR | 10-0768750 | 10/2007 |
| KR | 2008-0074286 A | 8/2008 |
| KR | 2011-0035805 A | 4/2011 |
| WO | 2018/043856 A1 | 3/2018 |

OTHER PUBLICATIONS

GenBank: EU249515.1, Corynebacterium ammoniagenes strain ATCC 6872 heat shock protein (hsp60) gene, partial cds, 1 page, Jul. 26, 2016.

* cited by examiner

*Primary Examiner* — Hope A Robinson
(74) *Attorney, Agent, or Firm* — Seed IP Law Group LLP (57) ABSTRACT

Provided are promoters and a method of producing L-amino acid using the same.

8 Claims, 3 Drawing Sheets
Specification includes a Sequence Listing.

PROMOTER AND USE THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_469USPC_SEQUENCE_LISTING.txt. The text file is 2.4 KB, was created on Jun. 24, 2020, and is being submitted electronically via EFS-Web.

TECHNICAL FIELD

The present disclosure relates to a novel promoter and a method of preparing a target product using the same.

BACKGROUND ART

Advances in understanding the intracellular mechanisms along with progress in technology have led the development of methods for producing various target products by regulating metabolisms of cells. Currently, microorganisms belonging to the genus *Escherichia* or the genus *Corynebacterium* have been used most frequently and directly to produce various low molecular or high molecular weight compounds, and protein drugs such as amino acids, polyphenols, flavonoids, antibodies, and natural rubbers.

Among a variety of methods of regulating the metabolisms, gene expression systems with high efficiency have been mainly studied to induce over-expression of target genes. For example, since promoters are well known as the most important factor involved in gene expression, extensive research using several promoters (Ptac, Ptrc, and Plac) derived from *E. coli* has been conducted. In addition, the applicant of the present disclosure found a cj1 promoter derived from *Corynebacterium ammoniagenes* exhibiting a strong activity of 296% of the activity of a tac promoter of *E. coli* through a previous study (Korean Patent Laid-Open Publication No. 10-2006-0068505). However, there is still a need to develop a method of efficiently producing a target product with a high yield.

DISCLOSURE

Technical Problem

As a result of intensive research to develop methods of efficiently producing a target product by increasing expression of a target gene, the present inventors have found that a novel promoter (cj2.2) by modifying the sequence of the existing cj1 promoter known highly active and have identified that the novel promoter has an activity greater than that of the cj1 promoter by about 3 times or more, thereby completing the present disclosure.

Technical Solution

An object of the present disclosure is to provide a polynucleotide having a promoter activity, including a polynucleotide sequence of SEQ ID NO: 1.

Another object of the present disclosure is to provide a vector including the polynucleotide having the promoter activity.

Still another object of the present disclosure is to provide a host cell into which the vector is introduced.

Still another object of the present disclosure is to provide a method of producing a target substance, the method including culturing the host cell; and recovering the target substance from the host cell or a culture medium in which the host cell is cultured.

Advantageous Effects

Since the novel promoter according to the present disclosure may be introduced into a microorganism resulting in an increase in an expression level and activity of a gene linked thereto, a target product affected by the promoter and the gene may be efficiently produced.

BEST MODE

Hereinafter, the present disclosure will be described in detail. Meanwhile, each description and embodiment disclosed in the present disclosure may be applied herein to describe different descriptions and embodiments. In other words, all combinations of various components disclosed in the present disclosure are included within the scope of the present disclosure. Furthermore, the scope of the present disclosure should not be limited by the detailed description provided below.

An aspect of the present disclosure provides a polynucleotide having a promoter activity, including a polynucleotide sequence of SEQ ID NO: 1.

As used herein, the term "promoter" refers to an untranslated nucleotide sequence including a binding site for a polymerase, located upstream a coding region, and having the activity of initiating transcription of a promoter-target gene into mRNA, i.e., indicates a region of DNA that leads to initiation of transcription of a particular gene when a polymerase binds thereto. The promoter may be located at the 5' region of an mRNA transcription initiation site.

In the present disclosure, the polynucleotide including the polynucleotide sequence of SEQ ID NO: 1 and having the promoter activity may be interchangeably used with "polynucleotide" or "cj2.2 promoter". Throughout the specification, all of the above-described terms may be used.

For the purpose of the present application, the polynucleotide may have a higher promoter activity than those of conventional promoters. In addition, the polynucleotide may not only increase an expression level of a target gene operatively linked to the polynucleotide in a desired host cell but also increase an expression level and activity of a protein encoded by the target gene in addition to the expression level of the target gene.

In addition, the polynucleotide may be used as a general-purpose promoter.

As used herein, the term "target gene" refers to a gene encoding a target protein whose expression level is to be increased, such as a gene involved in production of amino acids, without being limited thereto.

Specifically, the gene may be a gene encoding a protein involved in production of amino acids such as methionine or cysteine, more specifically, a gene encoding a methionine-converting enzyme involved in production of methionine or a cysteine-converting enzyme involved in production of cysteine, even more specifically a gene encoding O-acetyl-homoserine sulfhydrylase involved in production of methionine or O-phosphoserine sulfhydrylase (OPSS) involved in production of cysteine, and most specifically, metZ gene or Opss gene, without being limited thereto. Sequences of the respective genes are easily available from known database such as GenBank of the National Institute of Health (USA) by those skilled in the art.

In the present disclosure, the polynucleotide may include a nucleotide sequence of SEQ ID NO: 1.

Additionally, the nucleotide sequence according to the present disclosure may be modified by mutagenesis well known in the art such as direct evolution and site-directed mutagenesis.

Thus, the polynucleotide may include a polynucleotide having a nucleotide sequence with a homology of 60% or more, specifically 70% or more, more specifically 80% or more, even more specifically 83% or more, 84% or more, 88% or more, 90% or more, 93% or more, 95% or more, or 97% or more with the nucleotide sequence of SEQ ID NO: 1. In addition, it will be obvious that any polynucleotide having a polynucleotide sequence having the homology as described above and including a deletion, a modification, a substitution, or an addition of one or several sequences is within the scope of the present disclosure as long as the polynucleotide retains biological activities substantially identical or corresponding to those of the nucleotide sequence of SEQ ID NO: 1.

As used herein, the term "homology" refers to a degree of identity with a given nucleotide sequence and may be indicated as a percentage. Throughout the specification, a homologous sequence having the same or similar activity with the given nucleotide sequence is indicated as "% homology". The homology with the nucleotide sequence may be determined using any algorithm known in the art, e.g., BLAST (Refer to: Karlin and Altschul, Pro. Natl. Acad. Sci. USA, 90, 5873, 1993) or FASTA introduced by Pearson (Refer to: Methods Enzymol., 183, 63, 1990). Based on the algorithm BLAST, programs known as BLASTN or BLASTX have been developed.

The term "stringent conditions" refers to conditions which permit specific hybridization between polynucleotides. Such conditions are disclosed in detail in known documents. For example, the conditions may include performing hybridization between genes having a high homology, e.g., a homology of 60% or more, specifically 90% or more, more specifically 95% or more, even more specifically 97% or more, and most specifically 99% or more, without performing hybridization between genes having a homology lower than the above homologies, or performing washing once, specifically two or three times, under conventional washing conditions for Southern hybridization at a salt concentration and temperature of 60° C., 1×SSC, and 0.1% SDS, specifically 60° C., 0.1×SSC, and 0.1% SDS, and more specifically 68° C., 0.1×SSC, and 0.1% SDS. Hybridization requires that two nucleotides have complementary sequences, although bases may mismatch according to the degree of stringent conditions of hybridization. The term "complementary" is used to describe the relationship between nucleotide bases capable of hybridizing with each other. For example, with respect to DNA, adenosine is complementary to thymine, and cytosine is complementary to guanine. Thus, the present disclosure may include not only substantially similar polynucleotide sequence but also a polynucleotide fragment isolated but complementary to the entire sequence.

Particularly, the polynucleotide having a homology may be detected using the above-described conditions under hybridization conditions including a hybridization step at a Tm value of 55° C. Also, the Tm value may be 60° C., 63° C., or 65° C., but is not limited thereto, and may be appropriately adjusted by those skilled in the art according to the purpose. The degree of stringent conditions for hybridizing polynucleotide may depend on a length of the polynucleotide and a degree of complementarity and variables are well known in the art (Refer to Sambrook et al., supra, 9.50-9.51, 11.7-11.8).

Particularly, the expression "including the nucleotide sequence of SEQ ID NO: 1" does not exclude an addition, a deletion, and/or a modification of a nucleotide that may occur during ligation to a target gene using a restriction enzyme or the like when the polynucleotide is ligated to the target gene, as a promoter.

Also, the polynucleotide including the nucleotide sequence of SEQ ID NO: 1 and having the promoter activity may include any nucleotide sequence hybridized with a nucleotide sequence entirely or partially complementary to the nucleotide sequence of SEQ ID NO: 1 under stringent conditions to have the promoter activity according to the present disclosure, without limitation.

Another aspect of the present disclosure provides a vector including the polynucleotide having the promoter activity.

In this regard, the "promoter" is as described above.

As used herein, the term "vector", as an artificial DNA molecule including a genetic substance capable of expressing the target gene in an appropriate host cell, refers to a DNA product including: an appropriate gene expression regulatory sequence; and a nucleotide sequence of the target gene operatively linked thereto.

Specifically, the term "gene expression regulatory sequence" refers to a sequence including a polynucleotide having a promoter activity and capable of expressing a target gene operatively linked thereto.

Particularly, the gene expression regulatory sequence may further include an operator sequence for controlling transcription, a sequence encoding an appropriate mRNA ribosome binding site, and DNA for regulating termination of transcription and translation, in addition to the promoter for initiating transcription of the gene, but is not limited thereto. In addition, a regulatory sequence suitable for prokaryotes may include a promoter and a ribosome binding site, without being limited thereto. The polynucleotide having the promoter activity according to the present disclosure may constitute a sequence for regulating gene expression as described above according to the purpose by those skilled in the art.

In addition, the term "operatively linked" means functionally linked to the nucleotide sequence of the target gene such that the polynucleotide having the promoter activity initiates and mediates transcription of the target gene. Operative linkage may be obtained using a genetic recombination technique known in the art, and site-directed DNA cleavage and ligation may be performed using a restriction enzyme, a ligase, and the like, known in the art, without being limited thereto.

The vector as used herein may be any vector expressed in a host cell, without limitation, and the host cell may be transformed by using any vector well known in the art. Examples of common vectors may include plasmid, cosmid, virus, and bacteriophage in a natural or recombinant form.

For example, pWE15, M13, λLB3, λBL4, λIXII, λASHII, λAPII, λt10, λt11, Charon4A, and Charon21A may be used as a phage vector or a cosmid vector, and pBR-based, pUC-based, pBluescriptII-based, pGEM-based, pTZ-based, pCL-based, and pET-based vectors may be used as a plasmid vector.

In addition, an endogenous promoter of a chromosome may be replaced with the polynucleotide having the promoter activity according to the present disclosure using a vector used for insertion into the chromosome of the host cell. For example, pECCG117, pDZ, pACYC177, pACYC184, pCL, pUC19, pBR322, pMW118, pCC1BAC, pCES208, and pXMJ19 vectors may be used, but the present disclosure is not limited thereto.

In addition, insertion of the polynucleotide into the chromosome may be performed by any method known in the art, for example, homologous recombination.

Since the vector according to the present disclosure may be inserted into the chromosome by homologous recombination, the vector may further include a selection marker to identify insertion of the chromosome. The selection marker is used to select cells transformed by the vector, i.e., to identify whether the polynucleotide is inserted thereinto, and may be any marker that provides selectable phenotypes such as drug resistance, nutrient requirement, resistance to cytotoxic agents, or surface protein expression. Since only cells expression the selection marker are able to survive or to show different phenotypes in an environment treated with a selective agent, transformed cells may be selected thereby.

Another aspect of the present disclosure provides a host cell into which the vector is introduced.

In this regard, the "vector" is as described above.

As used herein, the term "host cell" refers to a transformant transformed by the vector including the polynucleotide.

Here, the term "transformation" refers to a process of introducing the vector including the polynucleotide having the promoter activity into the host cell in such a way that the target gene regulated by the polynucleotide is expressed in the host cell. Specifically, the host cell is not limited as long as the polynucleotide is introduced into the host cell and operates as a promoter therein, and accordingly expression of the target gene regulated by the polynucleotide is increased. For example, the host cell may be a cell of a microorganism, a plant, or an animal, specifically a microorganism of the genus *Escherichia* or the genus *Corynebacterium*, and more specifically *E. coli* as a microorganism of the genus *Escherichia*, without being limited thereto.

Methods for the transformation include any methods enabling introduction of the vector into the host cell and may be performed by suitable standard techniques well known in the art selected according to the host cell. For example, electroporation, calcium phosphate ($CaPO_4$) precipitation, calcium chloride ($CaCl_2$)) precipitation, microinjection, polyethylene glycol (PEG) method, DEAE-dextran method, cationic liposome method, and lithium acetate-DMSO method may be used, but the present disclosure is not limited thereto.

Another aspect of the present disclosure provides a method of producing a target substance including: culturing the host cell; and recovering the target substance from the host cell or a culture medium in which the host cell is cultured.

In this regard, the "host cell" is as described above.

In the present disclosure, the target substance may be an amino acid. Specifically, the amino acid may be L-amino acid unless otherwise stated and may be selected from the group consisting of glycine, alanine, valine, leucine, isoleucine, threonine, serine, cysteine, glutamine, methionine, aspartic acid, asparagine, glutamic acid, lysine, arginine, histidine, phenylalanine, tyrosine, tryptophan, proline and any combination thereof, without being limited thereto. More specifically, the amino acid may be, but is not limited to, methionine or cysteine.

As used herein, the term "culturing" refers to growing the host cell in an artificially adjusted appropriate environment. In the present disclosure, the method of producing the target substance using the host cell including the polynucleotide may be performed any method well known in the art. Specifically, the culturing may be performed continuously by a batch process, a fed-batch process, or a repeated fed-batch process, without being limited thereto. A culture medium used for the culturing needs to satisfy requirements of particular strains in an appropriate method. Examples of sugar sources that may be used in the culture medium include: saccharides and carbohydrates such as glucose, sucrose, lactose, fructose, maltose, starch, and cellulose, oils and fats such as soybean oil, sunflower oil, caster oil, and coconut oil, fatty acids such as palmitic acid, stearic acid, and linoleic acid, alcohols such as glycerol and ethanol, and organic acids such as acetic acid. These substances may be used alone or in combination, without being limited thereto.

Examples of available nitrogen sources may include peptone, yeast extracts, meat extracts, malt extracts, corn steep liquor, soybean meal, and urea or inorganic compounds such as ammonium sulfate, ammonium chloride, ammonium phosphate, ammonium carbonate, and ammonium nitrate. These nitrogen sources may also be used alone or in combination, without being limited thereto.

Examples of available phosphorus sources include potassium dihydrogen phosphate, dipotassium hydrogen phosphate, or corresponding sodium salts thereof. The culture medium may further include a metal salt necessary for growth such as magnesium sulfate or iron sulfate. Also, essential materials for growth such as amino acids and vitamins may be used in addition to the above substances. Moreover, proper precursors may be used in the culture medium. The above-described substances may be added to the culture medium during a culturing process in a batch process or continuous process suitable for the cultures.

While culturing the host cell, the pH may be adjusted using a basic compound such as sodium hydroxide, potassium hydroxide, and ammonia or an acidic compound such as phosphoric acid or sulfuric acid in an appropriate manner. Additionally, an antifoaming agent, such as fatty acid polyglycol ester, may be used to prevent foam generation. Oxygen or oxygen-containing gas (e.g., air) may be injected into the cultures to maintain an aerobic state.

The temperature of the cultures (culture medium) may generally be in the range of 20° C. to 45° C., specifically in the range of 25° C. to 40° C. The culturing may be continued until a desired yield of the target substance is obtained, specifically for 10 to 160 hours.

The target substance may be separated and recovered from the cultures (culture medium) by any method known in the art. The separation may be performed by centrifugation, filtration, chromatography, crystallization, and the like. For example, a supernatant obtained after removing biomass by centrifuging the cultures at a low speed may be subjected to ion exchange chromatography, but the present disclosure is not limited thereto.

The recovering may further include a purification process.

MODE FOR INVENTION

Hereinafter, the present disclosure will be described in more detail with reference to the following examples. However, these examples are for illustrative purposes only, and the present disclosure is not intended to be limited by these examples.

Example 1: Construction of Library of Recombinant Vector Variants Including cj1 Promoter Sequence In order to discover promoters capable of strongly inducing gene expression in microbial strains, a library of variants was constructed based on the cj1 promoter known to exhibit a high activity (Korean Patent Laid-Open Publication No. 10-2006-0068505).

Specifically, the library of variants was constructed using a recombinant vector pCL-cj1-gfp including the sequence of the cj1 promoter as a template. The library was constructed using an error-prone PCR kit (Clontech Diversify® PCR Random Mutagenesis Kit). Polymerase chain reactions (PCRs) were conducted using primers of SEQ ID NOS: 2 and 3 under the conditions where variations may occur. Conditions for resulting one variation per 1000 bp are as follows: after pre-heating at 94° C. for 30 seconds in the presence of 40 μM of dGTP (final rxn) without using $MnSO_4$ (8 mM), a process of maintaining at 94° C. for 30 seconds and then at 68° C. for 1 minute was repeated 25 times. PCT products obtained thereby were subjected to 25 cycles of a process including denaturation at 95° C. for 50 seconds using a mega-primer (125 to 500 ng), annealing at 60° C. for 50 seconds, and extension at 68° C. for 12 minutes, and then treated with DpnI to construct the library by transforming *E. coli* DH5α strains.

Example 2: Evaluation of Activity Intensity of Green Fluorescent Protein (GFP) of Recombinant Vector In order to evaluate the activities of recombinant vector variants of the library constructed in Example 1 above, activities of green fluorescent proteins (GFPs) were compared with each other.

Specifically, the library consisting of about 10,000 strains or more was inoculated onto an M9 medium and cultured at 37° C., at 900 rpm for about 24 hours. Cultured *E. coli* was centrifuged at 4000 rpm for 10 minutes to obtain strains and suspended in a phosphate buffered saline (PBS). Then, variants with high fluorescence intensity of green fluorescent protein (GFP) were selected by a fluorescence analyzer.

Figure 1:
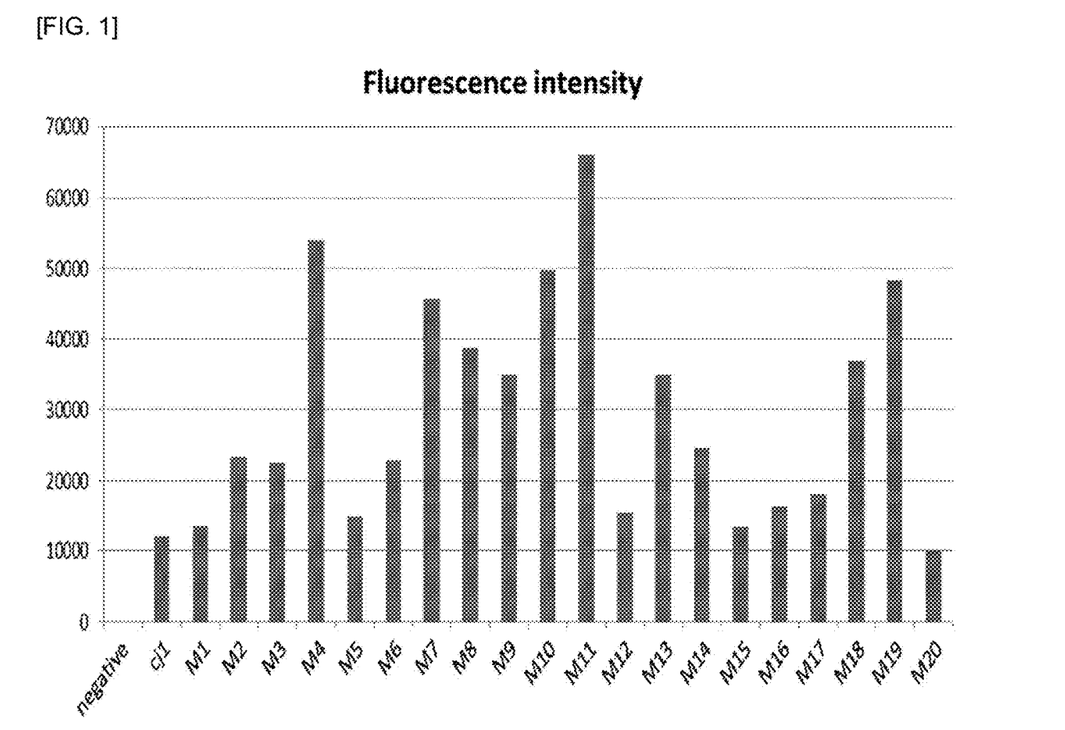
FIG. 1 is a graph illustrating analysis results of fluorescence intensities of green fluorescent proteins expressed in individual clones of a library of recombinant vector variants constructed according to an embodiment of the present disclosure, where cj1 is a clone including a cj1 promoter and M1 to M20 are individual clones of the library.

In a first screening, 20 variants having higher GFP activities than that of the cj1 promoter by about 1.1 times to 5 times were selected (FIG. 1). Among them, a promoter variant M11 having the highest GFP activity was named as cj2.2 promoter (SEQ ID NO: 1) and the sequence thereof was analyzed.

Example 3: Preparation of Expression Vector of Cj2.2 Promoter

Since it was confirmed that the cj2.2 promoter had the highest activity among the recombinant vector variants of the library in Example 2, site-directed mutagenesis was conducted using pCL_Pcj1 vector to introduce the cj2.2 promoter into microbial strains.

Specifically, PCR was performed using primers represented by SEQ ID NOS: 4 and 5. The PCR includes a process including denaturation at 94° C. for 30 seconds, annealing at 55° C. for 30 seconds, and extension at 68° C. for 12 minutes and this process was repeated 18 times.

Products obtained in the above process were treated with DpnI and DH5α strains were transformed thereby to prepare pCL_Pcj2.2 vector including the cj2.2 promoter.

Example 4: Measurement of Activity of Cj2.2 Promoter

Example 4-1: Measurement of Expression Level of Methionine Converting Enzyme (O-Acetylhomoserine Sulfhydrylase)

In order to identify the activity of the cj2.2 promoter and the ability to induce gene expression thereby, a methionine converting enzyme (O-acetylhomoserine sulfhydrylase) was ligated to the cj2.2 promoter and an expression level thereof was identified.

Figure 2:
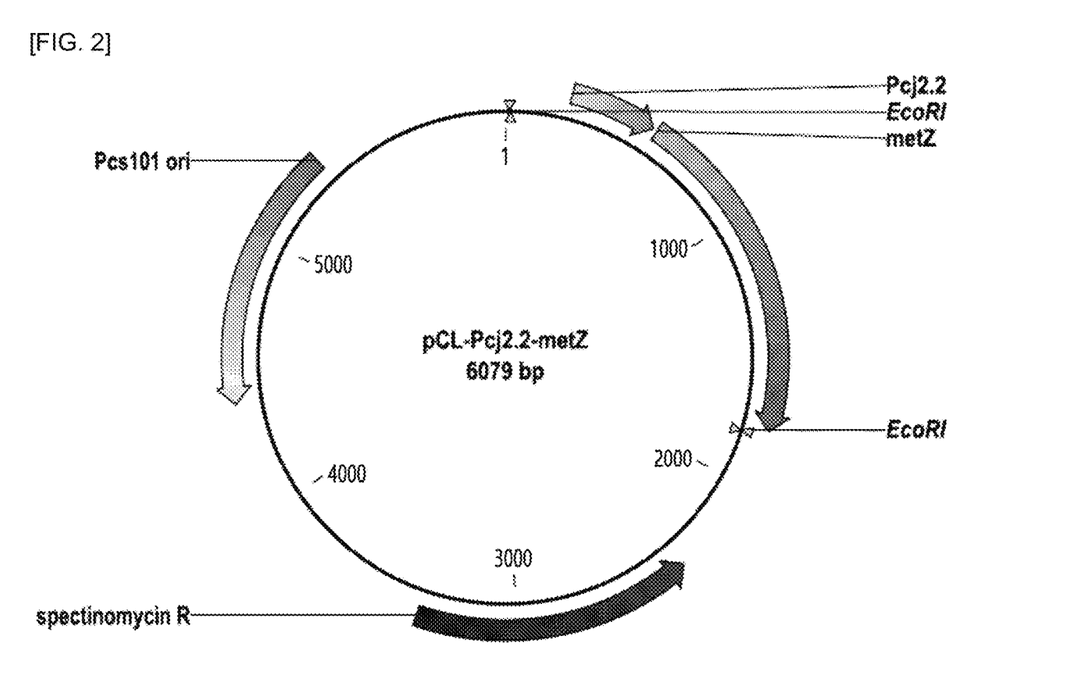
FIG. 2 is a cleavage map of a vector including a cj2.2 promoter and a metZ gene prepared according to an embodiment of the present disclosure.

Specifically, a metZ gene (Korean Patent Publication No. 10-1250651) encoding O-acetylhomoserine sulfhydrylase was cloned into the pCL_Pcj2.2 vector prepared in Example 3. PCR was performed using chromosome of *Rhodobacter sphaeroides* as a template and primers represented by SEQ ID NOS: 6 and 7, and 30 cycles of a process including denaturation at 94° C. for 30 seconds, annealing at 55° C. for 30 seconds, and extension at 72° C. for 2 minutes were repeatedly performed. DNA fragments obtained from the PCR were cleaved by BamHI/SalI and cloned into pCL_Pcj2.2 vector cleaved by the same restriction enzyme. The vector prepared as described above was named as pCL-Pcj2.2-metZ, and a schematic diagram of the vector is shown in FIG. 2.

*E. coli* K12 strains were transformed with the pCL-Pcj2.2-metZ vector and cultured in an LB plate medium supplemented with 50 μg/L of Spectinomycin to select colonies therefrom. The selected colonies were inoculated onto 3 ml of an LB medium supplemented with 50 μg/L of Spectinomycin and cultured at 37° C., at 200 rpm for 16 hours. Immediately after reinoculating the obtained products onto 25 ml of a new LB liquid medium (250 ml-flask) and culturing the products to have an $OD_{600}$ of 0.5 to 0.6 (for 2 to 3 hours) under the same culturing conditions, the products were cultured in 500 ml of a LB medium (1 L-vessel) supplemented with 4% glucose. After the culturing was completed, 1 ml of the culture medium was collected and a supernatant was removed by centrifugation to obtain cells. After washing the cells with a 0.1 M potassium phosphate buffer (pH 7.5), the cells were suspended with 1 ml of the potassium phosphate buffer and lyzed with a sonicator.

Then, the activity of the methionine converting enzyme (O-acetylhomoserine sulfhydrylase) contained in the lysates was measured. In order to measure the activity of the enzyme, 5 μl of the lysates were added to a mixed substrate solution in which 1 ml of O-acetylhomoserine (80 g/L), 0.01 ml of sodium methyl mercaptan (15%, w/v), 0.01 ml of O-acetylhomoserine sulfhydrylase, and 0.1 mM pyridoxal 5'-phosphate were mixed, and the mixture was stirred at 800 rpm at 33° C. to perform enzyme reactions. After the reactions were completed, the concentrations of methionine and O-acetylhomoserine were analyzed by HPLC, and protein activity was calculated by a conventional method using the analysis results of HPLC. The results are shown in Table 1 below.

TABLE 1

| Vector | Activity (Unit/mL) | Relative Activity |
|---|---|---|
| pCL-Pcj1-metZ | 9.3 | 1.0 |
| pCL-Pcj2.2-metZ | 29.2 | 3.1 |

As shown in Table 1, it was confirmed that the cj2.2 promoter according to the present disclosure increased the activity of O-acetylhomoserine sulfhydrylase by about activity 3.1 times more than that of the conventional cj1 promoter known to strongly induce gene expression in microbial strains.

Therefore, it was confirmed that the cj2.2 promoter has a stronger activity than conventional promoters, and accordingly the activity of the target enzyme encoded by a gene linked thereto may further be increased.

Example 4-2: Measurement of Expression Level of Cysteine Converting Enzyme (O-Phosphoserine Sulfhydrylase)

In order to identify the activity of the cj2.2 promoter and the ability to induce gene expression thereby, a cysteine converting enzyme (O-phosphoserine sulfhydrylase) was ligated with the cj2.2 promoter and an expression level thereof was identified.

Figure 3:
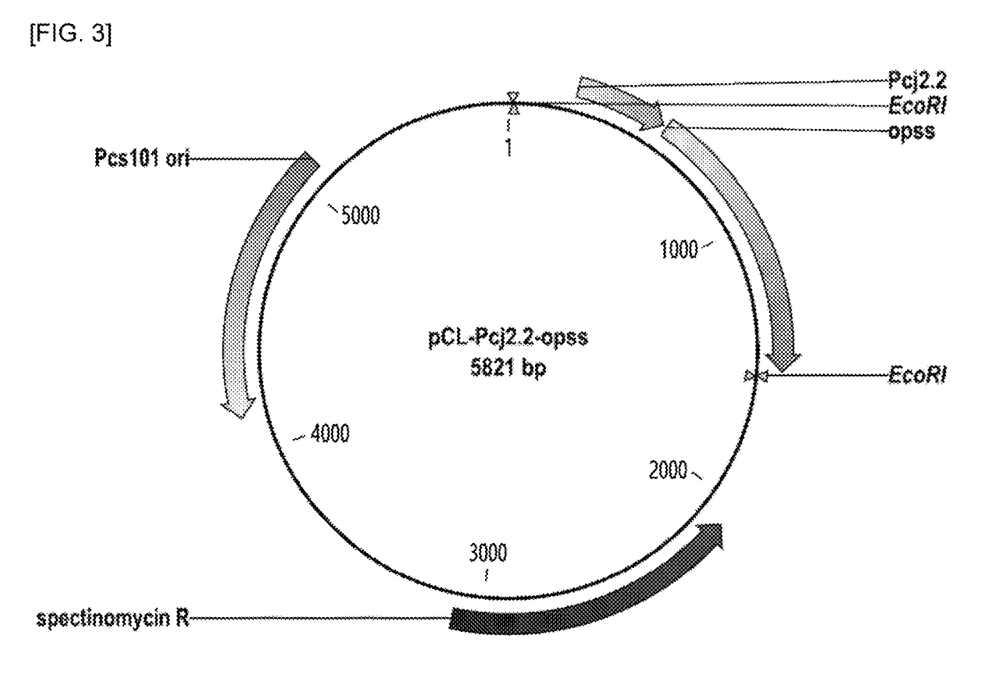
FIG. 3 is a cleavage map of a vector including a cj2.2 promoter and an opss gene prepared according to an embodiment of the present disclosure.

Specifically, O-phosphoserine sulfhydrylase (hereinafter, referred to as "OPSS", Korean Patent Publication No. 10-1208267) was cloned to the vector prepared in Example 3. PCR was performed using chromosome of *Mycobacterium* smegmatics as a template and primers represented by SEQ ID NOS: 8 and 9, and a vector was prepared in a manner similar to that of Example 4-1. The prepared vector was named as pCL-Pcj2.2-opss, and a schematic diagram of the vector is shown in FIG. 3.

*E. coli* K12 strains were transformed with the pCL-Pcj2.2-opss vector and cultured in an LB plate medium supplemented with 50 μg/L of Spectinomycin to select colonies therefrom. The selected colonies were inoculated onto 5 mL of an LB medium supplemented with 50 μg/L of Spectinomycin and cultured at 37° C., at 200 rpm for 16 hours. Immediately after reinoculating the obtained products onto 25 mL of a new LB liquid medium (250 ml-flask) and culturing the products to have an $OD_{600}$ of 0.5 to 0.6 (for 2 to 3 hours) under the same culturing conditions, the products were cultured in 500 mL of an LB medium (1 L-vessel) supplemented with 4% glucose until glucose was depleted. The cells were lyzed by adding 2% xylene (v/v) to the culture medium and the lysates were used for activity evaluation.

Then, the activity of OPSS enzyme obtained using the pCL-Pcj2.2-opss vector was evaluated according to a known method under the conditions disclosed in documents introduced by Mino K and Ishikawa K, FEBS letters, 551: 133-138, 2003; BurnsKE et al, J. Am. Chem. Soc., 127: 11602-11603, 2005; and Westrop G D et al, J. Biol. Chem., 281: 25062-25075, 2006). The substrate was added in a unit of mL, and the conditions for measuring the activity of the enzyme are shown in Table 2 below.

TABLE 2

| Enzyme | Blank — | OPSS Solution 40 mL of lysates (or 50 mg of crude protein) |
|---|---|---|
| 1M HEPES (pH 7.4) | 100 mL | 100 mL |
| 0.5M $Na_2S$ | 20 mL | 20 mL |
| 10 mM PLP | 20 mL | 20 mL |
| 100 mM OPS | 0 | 50 mL |
| DW | 790 mL | 750 mL |
| Total | 1000 mL | 1000 mL |

A mixture shown in Table 2 except for the enzyme was pre-incubated at 37° C. for 5 minutes, and 50 mg of the OPSS enzyme was added thereto, followed by reaction at 37° C. Then, 0.1 mL of 33.2% TCA was added to the reaction solution to terminate the reaction, and the reaction solution was diluted with 0.1 N HCl, followed by LC assay to analyze cysteine and cystine. The measured activities are shown in Table 3 below.

TABLE 3

| Vector | Activity (unit/mL) | Relative activity |
|---|---|---|
| pCL-Pcj1-opss | 6.0 | 1.0 |
| pCL-Pcj2.2-opss | 12.0 | 2.0 |

As shown in Table 3, it was confirmed that the cj2.2 promoter according to the present disclosure increased the activity of O-phosphoserine sulfhydrylase by about twice more than that of the conventional cj1 promoter known to strongly induce gene expression in microbial strains.

Therefore, it was confirmed that the cj2.2 promoter has a stronger activity than conventional promoters, and accordingly the activity of the target enzyme encoded by a gene linked thereto may further be increased.

Example 5: Production of Target Product Using Enzyme Obtained by cj2.2 Promoter

Example 5-1: Production of Methionine

Since it was confirmed that the activity of the methionine-converting enzyme (O-acetylhomoserine sulfhydrylase) was increased by using the cj2.2 promoter according to Example 4-1, the activity of the cj2.2 promoter and the efficiency of production of methionine in a reactor system were identified by producing the target product of methionine using the enzyme.

Meanwhile, O-acetylhomoserine sulfhydrylase converts O-acetylhomoserine into methionine.

Specifically, as a substrate of the enzyme reaction, O-acetylhomoserine produced by fermenting a microbial strain disclosed in Korean Patent No 10-1250651 was used. After removing cells from a cultured fermented broth using a centrifuge, 500 mL of the culture solution having a concentration of about 70 g/L was used as a substrate. As the enzyme O-acetylhomoserine sulfhydrylase, 50 mL of lysates (enzyme solution) obtained in Example 4-1 were used. 50 mL of sodium methyl mercaptan was used in the enzyme reaction, and pyridoxal 5'-phosphate (Sigma, USA) was added thereto in a concentration of 0.1 mM. The reaction was performed at a pH of 7.0, at 33° C., while stirring at 700 rpm. The reaction was conducted for 3 hours while supplying sodium methyl mercaptan thereto. Concentrations of O-acetylhomoserine and L-methionine were analyzed with time by HPLC, and the results are shown in Table 4 below.

TABLE 4

| Time [Minutes] | cj1 | | cj2.2 | |
|---|---|---|---|---|
| | O-acetylhomoserine [g/L] | L-methionine [g/L] | O-acetylhomoserine [g/L] | L-methionine [g/L] |
| 0 | 66.1 | 0 | 66.1 | 0 |
| 30 | 20.6 | 24.1 | 9.2 | 35.5 |
| 90 | 9.5 | 42.0 | 2.8 | 47.7 |
| 120 | 3.1 | 47.2 | 0 | 49.4 |
| 180 | 0 | 49.5 | — | — |

As shown in Table 4, it was confirmed that a conversion rate from o-acetylhomoserine into L-methionine using the cj2.2 promoter according to the present disclosure was higher than that using the conventional cj1 promoter known to strongly induce gene expression in microbial strains, and thus L-methionine was produced more quickly by the cj2.2 promoter.

This is because the activity of the target product encoded by the gene, i.e., the methionine converting enzyme (O-acetylhomoserine sulfhydrylase), was increased when the gene was expressed using the cj2.2 promoter according to the present disclosure.

Example 5-2: Production of Cysteine

Since it was confirmed that the activity of the cysteine converting enzyme (O-phosphoserine sulfhydrylase) was increased by using the cj2.2 promoter according to Example 4-2, the activity of the cj2.2 promoter and the efficiency of production of cysteine in a reactor system were identified by producing the target product of cystein using the enzyme.

Meanwhile, O-phosphoserine sulfhydrylase converts OPS into cysteine (or cystine that is an oxide of cysteine).

Specifically, the concentration of cystein of the conversion reaction solution was quantified by the Gaitonde method and LC assay. In addition, cystine produced as cysteine was oxidized was quantified by LC assay. First, prior to conversion reaction in a 1 L-vessel scale, an OPS fermented broth obtained by 1 L-vessel scale fermentation was centrifuged (at 10000 rpm, for 10 minutes, at 4° C.) to obtain a supernatant, and the supernatant was subjected to membrane permeation (0.45 μm) to remove strains. 72 g of $Na_2S$ was added to the OPS fermented broth (19.317 g/L), and precipitates obtained therefrom were removed using Whatman filter paper (6 μm). Then, 10 mM pyridoxal 5'-phosphate (PLP) was added thereto, and the mixture was pre-incubated at 37° C., at 200 rpm, for 5 minutes, and finally, 50 mg of OPS sulfhydrylase was added thereto to perform conversion reaction in the 1 L-vessel scale. Conditions for measuring enzyme activity are as shown in Table 5 below.

TABLE 5

| Composition of Reaction Solution | Concentration in Reaction Solution (or weight) | Mixed Amount (Weight or Volume) |
|---|---|---|
| OPS sulfhydrylase (2.59 μg/μl) | 50 mg | 19 mL |
| $Na_2S$ | 300 mM | 72 g |
| 10 mM PLP | 0.1 mM | 10 mL |
| OPS fermented broth from which strains are removed (19.317 g/l) | 104.42 mM | 1000 mL |
| Total | — | 1029 mL |

Then, 100 μL of the reaction solution was collected and mixed with 100 μL of 33.2% TCA at every 0, 10, 30, 60, and 120 minutes to terminate the reaction, and the reaction solution was diluted with 0.1 N HCl, followed by LC assay to analyze cysteine and cystine. Also, cysteine and cystine were quantified using the Gaitonde method. Analysis results are shown in Table 6 below.

TABLE 6

| Time | Cysteine and cystine [g/L] | |
|---|---|---|
| [Minutes] | Cj1 | Cj2.2 |
| 0 | 1.36 | 2.5 |
| 10 | 3.58 | 4.76 |
| 30 | 6.45 | 7.65 |
| 60 | 8.57 | 8.98 |
| 120 | 9.07 | — |

As shown in Table 6, it was confirmed that cysteine and cystine were produced more quickly using the cj2.2 promoter according to the present disclosure than using the conventional cj1 promoter known to strongly induce gene expression in microbial strains.

This is because the activity of the target product encoded by the gene, i.e., the cysteine converting enzyme (O-phosphoserine sulfhydrylase), was increased when the gene was expressed using the cj2.2 promoter according to the present disclosure.

The above description of the present disclosure is provided for the purpose of illustration, and it would be understood by those skilled in the art that various changes and modifications may be made without changing technical conception and essential features of the present disclosure. Accordingly, it is clear that the above-described embodiments are illustrative in all aspects and do not limit the present disclosure. The various embodiments disclosed herein are not intended to be limiting, with the true scope and spirit being indicated by the following claims. The present disclosure is to be limited only by the terms of the appended claims, along with the full scope of equivalents to which such claims are entitled.

The invention claimed is:

1. An isolated polynucleotide having a promoter activity, comprising the polynucleotide sequence of SEQ ID NO: 1, wherein SEQ ID NO:1 has an adenine nucleotide at position 286.

2. A vector comprising the isolated polynucleotide of claim 1.

3. The vector of claim 2, wherein the vector further comprises a gene encoding a target protein.

4. A host cell which comprises the polynucleotide of claim 1, wherein the host cell is a bacterial cell belonging to *Corynebacterium ammoniagenes* or *Escherichia coli*.

5. A method of producing a target substance, comprising: culturing the host cell of claim 4; and recovering the target substance from the host cell or a culture medium in which the host cell is cultured, wherein the host cell produces the target substance, and wherein the target substance is an amino acid.

6. A host cell, wherein the host cell is transformed with the vector of claim 2.

7. The host cell of claim 6, wherein the host cell is a bacterial cell belonging to *Corynebacterium ammoniagenes* or *Escherichia coli*.

8. A method of producing a target substance, comprising: culturing the host cell of claim 6; and recovering the target substance from the host cell or a culture medium in which the host cell is cultured, wherein the host cell produces the target substance, and wherein the target substance is an amino acid.

* * * * *

SEQUENCE LISTING

<160> NUMBER OF SEQ ID NOS: 9

<210> SEQ ID NO 1
<211> LENGTH: 307
<212> TYPE: DNA
<213> ORGANISM: Artificial Sequence
<220> FEATURE:

<223> OTHER INFORMATION: cj2.2 promoter

<400> SEQUENCE: 1

| caccgcgggc ttattccatt acatggaatg accaggaatg cagggaatg cgacgaaatt | 60 |
| gactgtgtcg ggagcttctg atccgatgct gccaaccagg agagaaaata atgacatgtg | 120 |
| caggcacgct ggtgagctgg agatttatga tctcaagtac cttttttctt gcactcgagg | 180 |
| gggctgagtg ccagaatggt tgctgacacc aggttgaggt tggtacacac tcaccaatcc | 240 |
| tgccgtcgcg ggcgcctgcg tggaacataa accttgagtg aaaccaaatc taggagatta | 300 |
| agatatc | 307 |

<210> SEQ ID NO 2
<211> LENGTH: 26
<212> TYPE: DNA
<213> ORGANISM: Artificial Sequence
<220> FEATURE:
<223> OTHER INFORMATION: error-prone F_PCR primer

<400> SEQUENCE: 2

| ttgcatgcct gcacaccgcg ggctta | 26 |

<210> SEQ ID NO 3
<211> LENGTH: 26
<212> TYPE: DNA
<213> ORGANISM: Artificial Sequence
<220> FEATURE:
<223> OTHER INFORMATION: error-prone R_PCR primer

<400> SEQUENCE: 3

| agtgaattcg agctcggtac ccgggg | 26 |

<210> SEQ ID NO 4
<211> LENGTH: 35
<212> TYPE: DNA
<213> ORGANISM: Artificial Sequence
<220> FEATURE:
<223> OTHER INFORMATION: cj2.2 site directed F_primer

<400> SEQUENCE: 4

| ataaaccttg agtgaaacca aatctaggag attaa | 35 |

<210> SEQ ID NO 5
<211> LENGTH: 35
<212> TYPE: DNA
<213> ORGANISM: Artificial Sequence
<220> FEATURE:
<223> OTHER INFORMATION: cj2.2 site directed R_primer

<400> SEQUENCE: 5

| ttaatctcct agatttggtt tcactcaagg tttat | 35 |

<210> SEQ ID NO 6
<211> LENGTH: 32
<212> TYPE: DNA
<213> ORGANISM: Artificial Sequence
<220> FEATURE:
<223> OTHER INFORMATION: metZ F_primer

<400> SEQUENCE: 6

| aattgtcgac atgggtaacg cgtttcgtga ag | 32 |

<210> SEQ ID NO 7
<211> LENGTH: 28

```
<212> TYPE: DNA
<213> ORGANISM: Artificial Sequence
<220> FEATURE:
<223> OTHER INFORMATION: metZ R_primer

<400> SEQUENCE: 7
aattggatcc tcagatcacc gcgagcgc                                              28

<210> SEQ ID NO 8
<211> LENGTH: 28
<212> TYPE: DNA
<213> ORGANISM: Artificial Sequence
<220> FEATURE:
<223> OTHER INFORMATION: OPSS F_primer

<400> SEQUENCE: 8
aattgtcgac atgacgcgct acgactcc                                              28

<210> SEQ ID NO 9
<211> LENGTH: 28
<212> TYPE: DNA
<213> ORGANISM: Artificial Sequence
<220> FEATURE:
<223> OTHER INFORMATION: OPSS R_primer

<400> SEQUENCE: 9
aattggatcc ttattccagc gcgtcctc                                              28
```